(12) United States Patent
Iltis

(10) Patent No.: US 11,703,605 B2
(45) Date of Patent: Jul. 18, 2023

(54) SYSTEM AND METHOD FOR IMAGING BY GAMMA RADIATION DETECTION

(71) Applicants: A.N.D.R.A., Chatenay-Malabry (FR); DAMAVAN IMAGING, Rosieres Pres Troyes (FR)

(72) Inventor: Alain Iltis, Troyes (FR)

(73) Assignees: A.N.D.R.A., Chatenay-Malabry (FR); DAMAVAN IMAGING, Rosieres Pres Troyes (FR)

(*) Notice: Subject to any disclaimer, the term of this patent is extended or adjusted under 35 U.S.C. 154(b) by 450 days.

(21) Appl. No.: 17/056,404

(22) PCT Filed: May 17, 2019

(86) PCT No.: PCT/EP2019/062805
§ 371 (c)(1),
(2) Date: Nov. 17, 2020

(87) PCT Pub. No.: WO2019/219912
PCT Pub. Date: Nov. 21, 2019

(65) Prior Publication Data
US 2021/0199821 A1 Jul. 1, 2021

(30) Foreign Application Priority Data
May 18, 2018 (FR) ...................................... 1854192

(51) Int. Cl.
*G01T 1/29* (2006.01)
*G01T 1/20* (2006.01)
(Continued)

(52) U.S. Cl.
CPC ............ *G01T 1/2978* (2013.01); *A61B 6/037* (2013.01); *G01N 23/20066* (2013.01); *G01T 1/20184* (2020.05); *G01T 1/2985* (2013.01)

(58) Field of Classification Search
CPC . G01T 1/2978; G01T 1/20184; G01T 1/2985; G01T 1/2907; G01T 1/29; A61B 6/037
See application file for complete search history.

(56) References Cited

U.S. PATENT DOCUMENTS

2021/0239862 A1* 8/2021 Petrak .................. G01T 1/2907

FOREIGN PATENT DOCUMENTS

DE    102019131695 A1 * 5/2021   ............. A61B 6/037
WO    2016185123 A1    11/2016
(Continued)

OTHER PUBLICATIONS

International Search Report from corresponding International Application No. PCT/EP2019/062805, dated Nov. 5, 2019, pp. 1-3, European Patent Office, Rijswijk, The Netherlands.
(Continued)

*Primary Examiner* — David P Porta
*Assistant Examiner* — Casey Bryant
(74) *Attorney, Agent, or Firm* — Hauptman Ham, LLP

(57) ABSTRACT

A system and method for imaging by gamma radiation detection having at least one processing unit analyzing at least one signal provided by at least one set of detection modules mounted on a frame and including, on the one hand, at least one module of Compton camera type having a field of view directed towards a volume delimited by the frame and, on the other hand, at least one pair of coincidence detection PET modules, diametrically opposite to each other on the frame and defining an imaging axis, the processing unit analyzing the signal derived from the Compton-type module to determine the intersection of the imaging axis with the field of view and to determine the optimal orientations and/or locations of the various detection modules on the frame so that the imaging axis passes through the source of the gamma radiation in the object to be imaged.

15 Claims, 5 Drawing Sheets

Figure 1:
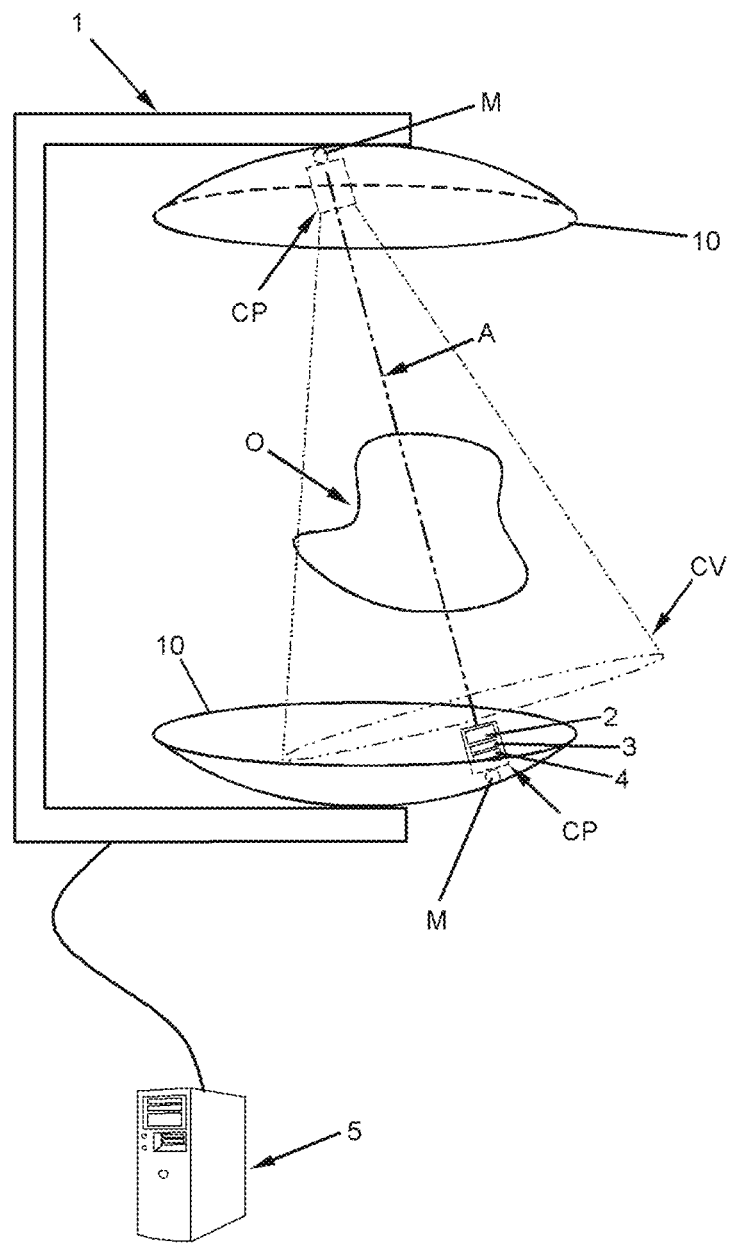

(51) Int. Cl.
*A61B 6/03* (2006.01)
*G01N 23/20066* (2018.01)

(56) References Cited

FOREIGN PATENT DOCUMENTS

| WO | WO-2016185123 A1 * | 11/2016 | ............ A61B 6/02 |
| WO | 2017025842 A1 | 2/2017 | |
| WO | WO-2017025842 A1 * | 2/2017 | ............ A61B 6/032 |
| WO | 2018019941 A1 | 2/2018 | |
| WO | WO-2018019941 A1 * | 2/2018 | ............ A61B 6/037 |
| WO | WO-2020032924 A1 * | 2/2020 | ............ A61B 6/037 |

OTHER PUBLICATIONS

Iltis et al., A. "Temporal Imaging CeBr 3 Compton Camera: A New Concept for Nuclear Decommissioning and Nuclear Waste Management," EPJ Web of Conferences, vol. 170, p. 06003, Jan. 10, 2018.

Braem et al., A. "Feasibility of a novel design of high resolution parallax-free Compton enhanced PET scanner iedicated to brain research," Physics in Medicine & Biology, vol. 49, No. 12, Jun. 21, 2004, pp. 2547-2562.

* cited by examiner

SYSTEM AND METHOD FOR IMAGING BY GAMMA RADIATION DETECTION

RELATED APPLICATIONS

The present application is a National Phase of International Application Number PCT/EP2019/062805, filed May 17, 2019, and claims priority to French Application No. 1854192, filed May 18, 2018.

TECHNICAL FIELD OF THE INVENTION

The present application relates to the field of imaging and more particularly to the imaging of gamma ray sources. Particularly, the invention relates to a system and methods for imaging by detection of gamma rays combining the detection of Compton camera type and the coincidence detection of Positron Emission Tomography (PET) type. The invention further relates to the use of the imaging and/or detection system in particular in the fields of astronomy, nuclear industry and medicine.

TECHNOLOGICAL BACKGROUND OF THE INVENTION

Currently, the imaging of gamma ray sources (whose energy is generally greater than 30 KeV) is mainly performed for medical diagnostic purposes around three techniques: PET, SPECT and Compton Camera.

The SPECT is based on scintigraphy and allows making three-dimensional images and reconstructions of the organs and their metabolism using a set of gamma cameras rotating around a patient. The SPECT can use several gamma ray energies, but the lead collimator that allows knowing the trajectory of the rays absorbs more than 99% therefrom.

The PET generally uses a ring of segmented detectors. For the PET, positron-emitting radio-pharmaceutical compounds are used. These give rise to a pair of 511 KeV photons, whose emission source can be located thanks to their simultaneous detection on the ring of detectors (coincidence detection). However, the radio-elements used for the PET have a short life and are therefore often expensive. The PET imaging is a functional imaging which is very attractive to guide a medical intervention with an image that clearly indicates where the observed radiation source is located. This is particularly the case in Oncology where the emission of the rays is concentrated on the tumors and allows differentiating these tumors from healthy tissues. In addition, PET imaging is also widely used in preclinical imaging on the rat or on mice to observe the biological processes in vivo. The PET imaging is, moreover, the imaging technology that allows obtaining the currently most accurate images (signal/noise ratio and angular resolution), for energetic gamma radiations of 511 KeV. Particularly, one of the key points in the PET imaging is the accurate measurement of the Time-of-Flight of the 511 KeV photons from their place of emission. This time-of-flight measurement is all the better the thinner the traversed scintillator thickness. However, in such configurations, a large part of the photons is not detected correctly because the probability of detection increases with the traversed scintillator thickness. However, the PET imagers usually consist of a complete ring around the patient (or any object) whose diameter is of about 80 cm, for a width of more than 20 cm and a scintillator thickness of 20 mm. This ring configuration is imposed by the very small field of view of the PET. Indeed, only the interactions in coincidence between two detectors are observed, which imposes a reduced solid angle. This configuration makes their use difficult to envisage in a context of a surgical operation. In addition, the PET scanners are very expensive (on the order of two million Euros) due to the volume of detectors required. On the other hand, in the context of the preclinical imaging where the dimensions of the scanner are much smaller, the doses of radioactivity injected into the mice are very high, which can disrupt the physiological processes wished to be observed. Likewise, for interventional imaging, it would be interesting to be able to drastically reduce the dose injected (for example a dose less than or equal to 1 MBq) in the vicinity of the organ to be treated.

The Compton camera, like the SPECT, allows making an image whatever the energy of the gamma radiation, but unlike the SPECT, all the photons can contribute to the image. However, the applications of the Compton camera are still often limited today, in particular because of its cost, the high level of noise and the difficulty of obtaining accurate reconstructions. More generally in all the technologies above, when scintillating crystals are used to make an image of gamma radiation sources, the probabilistic nature of the gamma photon/matter interaction is encountered. Two effects are essentially noticed. The first effect lies in the fact that the gamma photon can be absorbed at any depth on its propagation path ("Depth of Interaction" effect). The second effect is that all current imaging systems (pixel array or Anger camera) are based on the postulate that the place where the maximum light emission takes place is the place where the gamma photon has been detected. Because of the Compton deviation, this assumption is correct as long as the mean value of a large number of events is considered. On the other hand, in the case of a PET-type scanner, if the position of a single event is reconstituted, the error, on the position, can be of several millimeters. The solution adopted is then to reject the events for which the energy deposited is not correct. This leads to rejecting a large number of events. Solutions called "temporal imaging" solutions have therefore been developed, as described in particular in French patent applications FR2997766 and FR3013125 with regard to the PET. In addition, concerning the technology of the Compton cameras, patent applications WO2016185123 and WO2017077164 describe systems and methods that benefit both from the temporal imaging, but also from the combination of the Compton imaging and PET imaging. The present application therefore proposes solutions to overcome some of the drawbacks of the prior art, in particular by aiming to provide, preferably at lower cost, devices, systems and methods whose use is as varied as possible and/or which allow improving the quality of the images obtained.

Moreover, another general and constant problem in the field concerns the measurement of the time of arrival of the first photons on a given pixel, because it is important for the quality of the images obtained using the signals collected by the PET scanners and also for the temporal Compton cameras. Particularly, the first photon detected in a crystal allows measuring the temporal coincidence for an emission at 511 KeV and therefore allows estimating the Time-of-Flight of the photons from the source. In addition, in a temporal imaging logic, the time of arrival of the first photons on each pixel allows determining the position of the disc (and therefore of the cone) of the non-scattered photons, which allows improving the accuracy of the estimation of the position (particularly in "depth", that is to say parallel to the imaging axis on which the detectors PET are aligned).

The use of monolithic crystals for PET scanners has multiple advantages, such as an easy access to the depth measurement, a reduced cost and a potential for high spatial resolution, in particular by using information relating to the distribution of events over time ("temporal imaging", as mentioned above). The fastest scintillating crystals are today Lanthanum halides, such as for example CeBr3 or LaBr3: which emits up to 4 times more photons during the first nanosecond than the LYSO: This is currently often used in the field. As such, these lanthanum halides are the best candidates for the temporal imaging. However, these crystals are very delicate to implement because they are extremely sensitive to atmospheric conditions (in particular hydrometry), which restricts their use in the form of monolithic crystals.

However, the use of monolithic crystals faces a paradox when it comes to the measurement of the time of arrival of the photons. Indeed, a priori, the measurement of the time of arrival of the first photons should be more accurate in a monolithic crystal than in a detector in the form of an array (i.e., pixel array) of scintillating crystals, in particular due to the absence of optical deviation from the place of emission. However, in a "pixelated" detector, the first photon detected by a given pixel is very likely to have undergone multiple reflections on the lateral faces of the crystal before being collected by the photodetector and the information on the real time of emission will therefore be inaccurate, even totally lost. On the other hand, in a monolithic crystal, once the position of the interaction is known, it is possible to determine a "disk of non-scattered photons" in which the majority of the photons detected have not undergone any disturbance (e.g., reflection) between their points of emission in the source and their collection points in the photo-detector. The arrival time is therefore more accurate. Today, however, the temporal resolutions measured with monolithic crystals are lower than those measured with pixel arrays.

The present application therefore also proposes solutions to this paradoxical problem.

GENERAL DESCRIPTION OF THE INVENTION

An aim of the present invention is to overcome at least some drawbacks of the prior art by proposing a gamma ray imaging system which is space-saving and which can be used under many conditions, in particular in preclinical imaging or in clinical imaging of a specific object or organ, or even to perform imaging-guided biopsies.

This aim is achieved by a system for imaging by gamma radiation detection comprising at least one processing unit analyzing at least one signal provided by at least one set of detection modules mounted on at least one frame, each of the modules comprising at least one scintillator emitting photons, when subjected to the influence of said gamma radiation, at least one photo-detector generating said signal in response to said photons emitted by said scintillator and at least one acquisition device which collects said signal to transmit it to said processing unit, the system being characterized in that:

said frame comprises a plurality of locations distributed along at least one portion of two spherical caps facing each other and defining an imaging volume inside the system, said caps being separated by a distance that allows accommodating an object to be imaged in said volume;

said frame being open, on at least one side between the two caps, so as to leave free access to said object to be imaged in said volume;

said set of detection modules includes at least one module of Compton camera type, having a field of view directed towards a volume delimited by said frame, and whose scintillator comprises at least one plate of scintillator crystal, called fast scintillator crystal, whose time of rise to the light peak is less than 1 ns, so that this module is able to produce an image by using Compton scattering;

said set of detection modules includes at least one pair of coincidence detection PET modules, diametrically opposite to each other on said frame, each on one of the two caps, and defining an imaging axis.

said processing unit analyzes the signal derived from said Compton-type module to determine the intersection of said imaging axis with said field of view and to determine the optimal orientations and/or locations of the various detection modules within said caps of the frame so that the imaging axis passes through the source of said gamma radiation in said object to be imaged.

According to another feature, the system includes at least one motor, driven by said processing unit and controlling the mobility of at least one of said detection modules on said frame and/or of the object to be observed inside said volume to obtain said orientations and/or said optimum locations defined by said processing unit.

According to another feature, at least one of said sets of detection modules actually includes only two modules, thanks to a first module, called "hybrid" module, whose scintillator comprises at least one plate of scintillator crystal, called fast scintillator crystal, whose time of rise to the light peak is less than 1 ns, called "hybrid" module being able to produce both a Compton scattering and an absorption of at least part of the gamma radiation for a detection of coincidence between the events in this first hybrid module and the events in a second detection module with which this first hybrid module therefore forms said pair of coincidence detection PET modules.

According to another feature, said second detection module of each set is either also a hybrid module or a module called "PET" module, able to produce only a photoelectric absorption for a detection of coincidence of events compared to the other detection module with which it forms said pair of coincidence detection PET modules.

According to another feature, each set includes several second modules facing the first hybrid module which is orientable by said motor to align the imaging axis between said hybrid module and either of these second modules.

According to another feature, said motor is able to move at least said second module on said frame, to place it facing the first hybrid module which is oriented by said motor to align the imaging axis between the first and the second module.

According to another feature, the first and the second module are both hybrid modules, at least one of which is orientable and at least one of which is movable on the frame, by said motor.

According to another feature, said signal processing unit analyzes the signals derived from each set of detection modules and determines both the Compton scattering events and the photoelectric absorption events, to obtain the three-dimensional position, the energy and the time sequence of the Compton and photoelectric interactions of the gamma radiation in the volume between the detection modules of each set.

According to another feature, the signal processing unit measures, in the signal derived from the hybrid module, a time threshold of coincidence in a time window smaller than the maximum time of transfer of the light in the hybrid module, inside the single plate or between the plates and, to identify valid Compton events.

According to another feature, the processing unit calculates the Time-of-Flight of the photons between the two modules of the PET module pair, first hybrid module and second module, to measure the depth of the source of gamma radiation in the object to be imaged.

According to another feature, the processing unit uses the signal of at least one module pair of Compton camera type to combine their Compton imaging and carry out a triangulation in order to measure the depth of the source of gamma radiation in the object to be imaged.

According to another feature, the system is characterized in that:
  said scintillator is a monolithic scintillator crystal;
  said photo-detector is an analog photo-detector whose analog signal provides a measurement representative of the energy of the photons emitted by said monolithic scintillator over time;
  said acquisition device is configured for the detection and the filtering of the scintillation events thanks to an algorithm allowing it to measure a first time at which said analog signal exceeds a first threshold representative of the first detected photon and to measure a second time at which said analog signal exceeds a second threshold representative of a number n of detected photons, then to calculate the period that separates the first and the second time.

According to another feature, said acquisition device collects the signal from the scintillator on a plurality of pixels and compares the time of the first photon detected on each of the i pixels, in order to determine the minimum value of this time on all the pixels and thus to estimate the time of arrival of the first photon emitted by the scintillator.

According to another feature, said acquisition device calculates a slope of rise of the signal between the two thresholds and eliminates the detected events whose rise slope is less than a determined value, in order to eliminate the signal noise and to keep only validated scintillation events.

According to another feature, said processing unit establishes a map of the time of arrival of the photons from the events filtered by said acquisition device to provide a first estimation of the position of a scintillation event and of a disc of non-scattered photons, then compares at least one model of law of emission of the photons by the scintillator with the number of photons detected in this disk at different times after the arrival of the first photon, in order to correct the diameter of this disk accordingly and therefore improve the accuracy of the measurement of the depth of the event.

According to another feature, the processing unit corrects the probable delay between the measured and actual values of the time of arrival of the first photon, by comparing these measured values with at least one model of laws of emissions of the photons by the scintillator, preferably by taking into account the measurements of the times of arrival of the first and $n^{th}$ photon in the adjacent pixels.

DESCRIPTION OF THE ILLUSTRATIVE FIGURES

Figure 2:
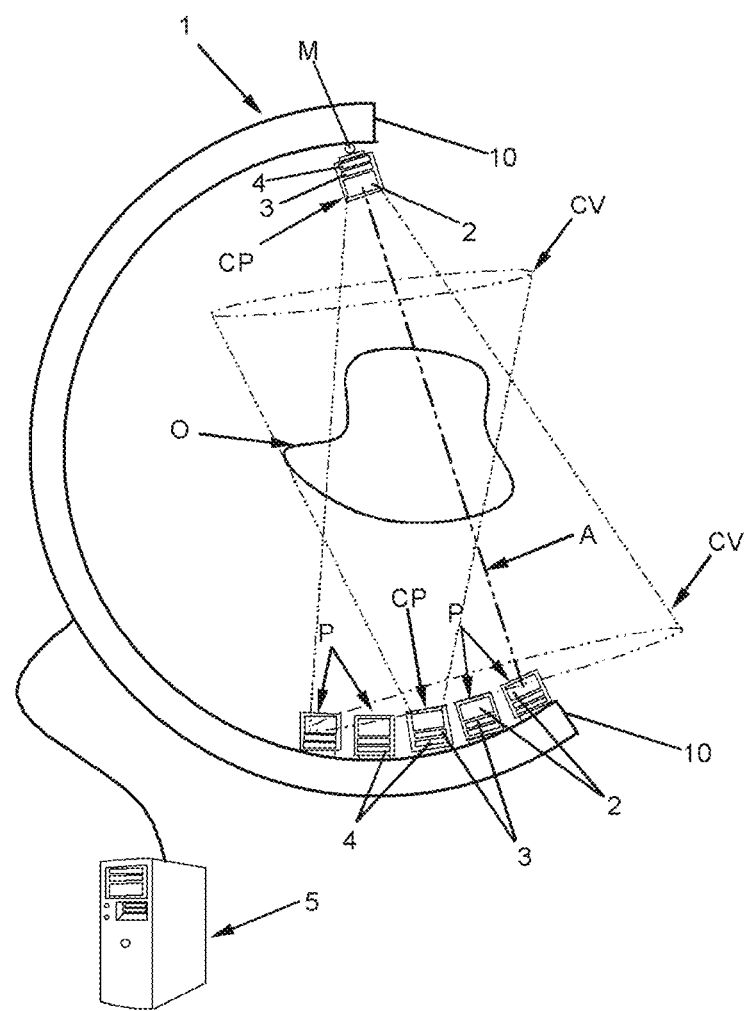
Figure 4:
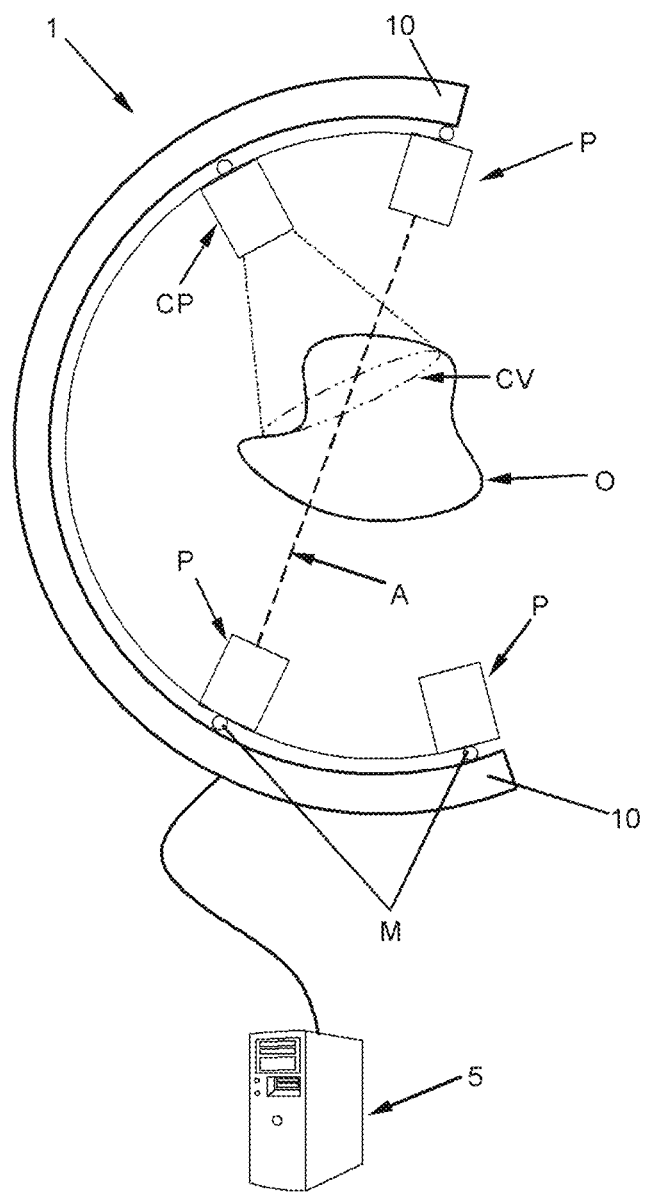
Figure 5:
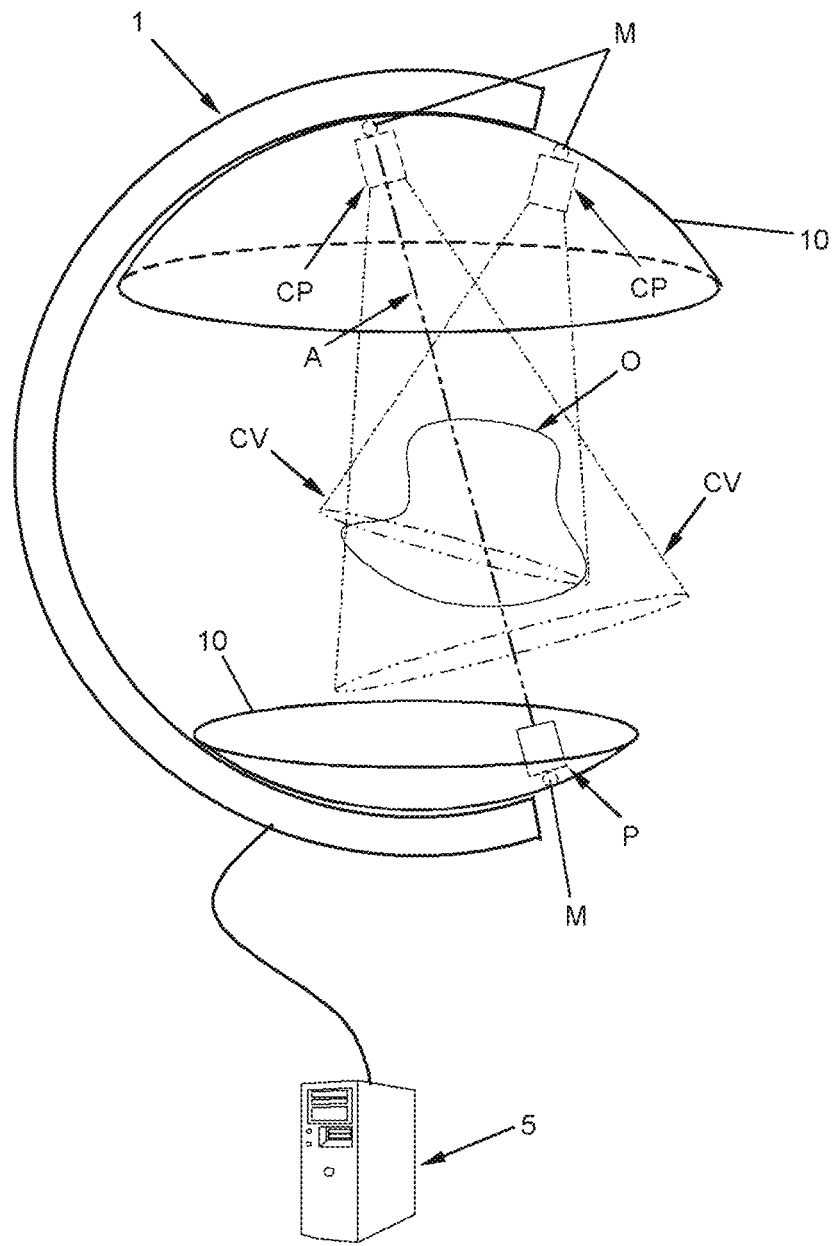

Other features and advantages of the present invention will emerge more clearly upon reading the description below, given with reference to the appended drawings, in which:
  FIG. 1 represents a perspective view of an imaging system according to some embodiments;
  FIG. 2 represents a perspective view of an imaging system according to other embodiments;
  FIGS. 3A, 3B, 3C and 3D represent schematic views in transparency of the composition of various detection modules which can equip imaging systems according to various embodiments, while FIGS. 3E and 3F represent photon detection curves, with the time on the abscissa and the energy on the ordinate;
  FIG. 4 represents a perspective view of an imaging system according to some embodiments;
  FIG. 5 represents a perspective view of an imaging system according to other embodiments;

DESCRIPTION OF THE PREFERRED EMBODIMENTS OF THE INVENTION

The present invention relates to a system and a method for imaging by gamma radiation detection comprising at least one processing unit (5) analyzing at least one signal provided by at least one set of detection modules (CP, P) mounted on a frame (1) and including, on the one hand, at least one module of Compton camera type having a field of view (CV) directed towards a volume delimited by the frame and, on the other hand, at least one pair of coincidence detection PET modules, diametrically opposite to each other on said frame and defining an imaging axis (A), said processing unit (5) analyzing the signal derived from said Compton-type module to determine the intersection of said imaging axis (A) with said field of view (CV) and determine the optimal orientations and/or locations of the various detection modules (CP, P) on the frame so that the imaging axis (A) passes through the source of said gamma radiation in said object (O) to be imaged. Thus, it is understood that there is a benefit from the wide field of view (CV) of the Compton camera (angular opening of about 45° in general) to locate the source of the gamma radiation (with an angular accuracy on the order of 5° most often) and this information is used to position the modules to be used in PET mode in order to acquire a more accurate image (in a smaller line of sight/imaging). In a manner known per se, each of the detection modules comprises at least one scintillator (2) emitting photons when it is subjected to the influence of said gamma radiation, at least one photo-detector (3) generating said signal (S) in response to said photons emitted by said scintillator (2) and at least one acquisition device (4) collecting said signal to transmit it to said processing unit (5). The Compton-type module preferably includes a scintillator (2) that comprises at least one plate of scintillator crystal (P1), called fast scintillator crystal, whose time of rise to the light peak is less than 1 ns, so that this module is able to produce an image by using the Compton scattering. More specifically, said frame (1) is open, on at least one side between the two caps (10), so as to leave free access to said object (O) to be imaged in said volume.

In some embodiments, said frame (1) comprises a plurality of locations distributed along at least one portion of two spherical caps (10) facing each other and defining an imaging volume inside the system, said caps (10) being separated by a distance (D) that allows accommodating an object (O) to be imaged in said volume. The PET modules of the pair of coincidence detection modules are therefore mounted diametrically opposite to each other on said frame, each on one of the two caps (10).

Thus, it is therefore understood that the present system uses the Compton camera to find the area of interest (gamma radiation source) in the object (O) to be imaged and that the processing unit determines the position of the PET modules allowing the imaging axis (A) to pass through this area, in order to make an accurate image, in PET (coincidence detection) mode in two dimensions of this area of interest. It is therefore understood that the frame defines a volume between two caps (or arcs of circles, or even elliptical arcs) and has an opening on at least one side of the frame through which the object remains accessible (and can be introduced into said volume) and that, inside this volume, it is possible to restrict the field covered by the detection modules. Such a system can advantageously be used to make preclinical imaging or for clinical imaging of a specific organ or even to perform imaging-guided biopsies. One of the objectives targeted by the objects of the present application also relates to the fact of being able to make locally accurate images of a large object (or subject), such as a human or a large animal (pig, horse for example) and the imaging made via the Compton cameras (C, CP) gives an image with a wide field of view and moderate resolution. The areas of interest are then detailed by moving the coincidence detectors to obtain an accurate image within their field of view which is more limited in size.

The term "spherical" actually designates in the present application a geometric disposition which may be slightly elliptical, as long as it is possible to have the modules facing each other, with a common axis of symmetry adapted to a PET mode coincidence detection. The expression "at least one spherical cap portion", relating to the distribution of the locations of the modules, covers of course definitions such as caps disposed at two opposite poles of a ball (e.g., spherical or elliptical ball) or slightly eccentric caps but having, two by two, diametrically opposite locations or at least facing each other. In addition, this expression "at least one spherical cap portion" covers not only opposite and identical spherical caps, for example as illustrated in FIG. 1, or opposite caps but of different sizes, for example as illustrated in FIG. 5, but it actually also covers, (by the word "portion") in the present application, distributions of the locations only according to arcs (arcs of circles or elliptical arcs) facing each other, for example as represented in FIG. 2 or FIG. 4. Indeed, the frame (1) can actually cover a single plane or several planes and it can for example be limited to a C-shape or even define only two arcs defining said locations and kept separate from each other by any structure complying with said distance (D) and providing an opening that offers said free access to said object (O) to be imaged. Thus, various embodiments provide a wide range of products starting from very simple, light and economical systems substantially in only 2 dimensions, up to more complex systems covering 3 dimensions and facilitating setting up the imaging thanks to their complete configuration, advantageously driven by said processing unit. The term "events" relating to the detection modules is perfectly known to those skilled in the art and designates the interaction of an ionizing radiation with a material called "scintillating" or "scintillator" material that emits at least one photon when a particle collides with one of the atoms constituting it. The terms "Compton scattering" or "Compton camera" are known to those skilled in the art and of course relate to the detection of two events that are very close in time and that are detected by a single scintillator or two scintillators close to each other, as detailed for example in the application WO2016185123. The terms "PET module" or "in PET mode" or "coincidence detection" are also known to those skilled in the art and of course designate the fact that the time separating events that occur between two diametrically opposite scintillators around the gamma radiation source is measured.

In some embodiments, the system includes at least one motor (M), driven by said processing unit (5) and controlling the mobility of at least one of said detection modules (CP, P) on said frame and/or of the object to be observed inside said volume in order to obtain said orientations and/or said optimum locations defined by said processing unit (5). It is therefore understood that various embodiments provide at least one motor to be able to move the object to be imaged (O) according to the positions of the detection modules determined by the processing unit and/or at least one motor (M) also allowing to control the relative orientation and/or the relative displacement of the modules, in order to align the imaging axis with the area of interest, inside at least part of said volume. Thus, by moving and/or orienting at least one module or several modules, the processing unit allows the modules to be aligned with an area of interest, preferably targeted beforehand by a Compton or hybrid module. Various embodiments therefore provide displacement arrangement for moving the object in at least a portion of the volume inside the frame and/or displacement arrangement for moving at least one of the modules on the frame. The term "motor" is used in the present application according to its general meaning actually designating the function of controlling a movement, regardless of the type of movement concerned, which possibly involves a pivoting about an axis to define an orientation, as well as a displacement in two or three dimensions, but also a combination of these two types of movements. Those skilled in the art will more easily appreciate the scope upon reading the definitions provided below and the various illustrative embodiments resulting therefrom.

In some embodiments, at least one of said sets of detection modules (P, CP) actually includes only two modules, thanks to a first module (CP), called "hybrid" module, whose scintillator (2) comprises at least one plate (P1) of scintillator crystal called fast scintillator crystal, whose time of rise to the light peak is less than 1 ns, called "hybrid" module being able to produce both a Compton scattering and an absorption of at least part of the gamma radiation for a detection of coincidence between the events in this first hybrid module (CP) and the events in a second detection module (CP, P) with which this first hybrid module (CP) therefore forms said pair of coincidence detection PET modules. It is therefore understood that, in some embodiments, the system takes advantage of the possibility of having a hybrid module forming both the Compton camera and one of the PET modules of the pair of coincidence detectors. Thus, instead of having three modules within each set, it is possible to have only two (including a hybrid module) or to have a three-module set and a two-module set. In addition, it is of course possible to have at least a first "mixed" Compton-PET set (with three modules or with two modules, including a hybrid module), combined with at least another set including only two coincidence detection PET modules and therefore benefiting from the Compton module of the first set.

In some embodiments, said second detection module (CP, P) of each set is either also a hybrid module (CP) or a module (P) called "PET" module, able to produce only one photoelectric absorption for a detection of coincidence of events compared to the other detection module with which it forms said pair of coincidence detection PET modules. Examples of these variants are shown in FIGS. 1, 2, 4 and 5. In some embodiments, each set includes several second modules (CP, P) which can be stationary (i.e., immobile) and which are disposed facing the first hybrid module (CP) which is orientable by said motor (M) to align the imaging axis (A) between said hybrid module (CP) and either of these second modules (CP, P). An example of this type of configuration is represented in FIG. 2. This type of configuration has the advantage of limiting the cost of the motor (M) to be used, but often requires an increase in the number of detection modules. In some embodiments, said motor (M) is able to move at least said second module (CP, P) on said frame (1), to place it facing the first hybrid module (CP) which is oriented by said motor (M) to align the imaging axis (A) between the first and the second module. In some embodiments, the first and the second module are both hybrid modules (CP), at least one of which is orientable and at least one of which is movable on the frame (1), for example said motor (M). Thus, the movable hybrid module (equipped with a displacement motor) can be placed in front of the orientable hybrid module so that the PET imaging axis is optimal according to the Compton imaging in the field of view (CV). It will be noted that, when several modules facing a hybrid module are provided, as for example represented in FIG. 2, it is not necessarily required for the second hybrid module to be movable since the imaging axis (A) in PET can be determined with one of the other modules. In addition, the use of two Compton modules (whether hybrid or not and in whatever configuration, as for example in FIG. 1, 2 or 5) allows a triangulation to estimate the depth of the radiation source, as detailed below.

In some embodiments, said signal processing unit (5) analyzes the signals derived from each set of detection modules (CP, P) and determines both the Compton scattering events and the photoelectric absorption events, to obtain the three-dimensional position, the energy and the time sequence of the Compton and photoelectric interactions of the gamma radiation in the volume between the detection modules (CP, P) of each set. In some embodiments, the signal processing unit (5) measures, in the signal derived from the hybrid module (CP), a time threshold of coincidence in a time window smaller than the maximum time of transfer of light in the hybrid module, inside the single plate (P1) or between the plates (P1) and (P2), to identify valid Compton events. Such a use has already been described in the application WO2016185123 and WO2017077164 and it is therefore not necessary to describe it in more detail.

In some embodiments, the processing unit calculates the Time-of-Flight of the photons between the two modules of the PET module pair, first hybrid module (CP) and second module (CP, P), to measure the depth of the source of gamma radiation in the object (O) to be imaged along the imaging axis. This calculation of the Time-of-Flight allows indeed measuring the depth of the source of the gamma radiation, as for example described in the patent applications "Time-of-Flight PET" By Joel S. Karp, PET center of excellence newsletter, Volume 3, Issue 4 FALL 2006; SNM advancing molecular imaging & therapy (in the 4 first paragraphs, particularly). This Time-of-Flight can be calculated between two modules of a pair of modules in PET mode, regardless of the type of modules of this pair, whether it is a first hybrid module (CP) and a second PET module (P) or two PET modules (P) or even two hybrid modules (CP). In some embodiments, the processing unit uses the signal of at least one module pair of Compton camera type to combine their Compton imaging and carry out a triangulation in order to measure the depth of the source of gamma radiation in the object (O) to be imaged. Thus, in the embodiments in which said set of detection modules includes two PET modules and at least one Compton module, as for example in FIG. 4, the Compton module allows a triangulation in combination with the imaging axis of the pair of PET modules for a first estimation of the depth, but the pair of PET modules allows specifying the depth thanks to the "Time-of-Flight". In addition, in some embodiments, it is provided to have two Compton modules, for example located on the same side of the object (O), in particular with two hybrid modules as in the example represented in FIG. 5 or with a Compton module next to a hybrid module and in front of a PET or Compton module according to various alternative embodiments. In all these various alternative embodiments with several Compton modules, the processing unit (5) will therefore be capable of using the Compton imaging signals to carry out a triangulation in order to measure the depth. Advantageously, by combining at least one pair of Compton modules with at least one pair of PET modules, it is possible to refine the measurement of the depth. It will be understood from the various variants described here that these pairs of Compton and PET modules may actually include a module in common (thanks to at least one hybrid module). In addition, in the case where two hybrid modules are used, this combination between the measurement of the Time-of-Flight and the Compton triangulation can advantageously be carried out from the signals of the same pair of hybrid modules, such as for example those in FIG. 1, but preferably after displacement of the pair of hybrid modules in order to optimally combine their signals in PET mode and their signals in Compton mode.

In some embodiments, the signal processing unit performs a Compton imaging from events whose energy is not of 511 keV (in particular to compensate for the fact that the PET imaging does not provide sufficient information to estimate the depth of the radiation source and detects only 511 keV events in coincidence on two diametrically opposite modules. In addition, in some embodiments, it is possible to perform injections of several different radios-elements to obtain a differential imaging and/or an injection of a radio-element generating events of at least two different levels of energy (such as for example the Na22 which generates 511 keV events and 1.3 MeV events).

In some embodiments, the hybrid module (CP) includes a single scintillator crystal plate (Pc, FIG. 3B) having a thickness greater than or equal to the mean free path of the gamma ray in the crystal considered, preferably greater than 5 mm. Such a hybrid module is known from the prior art and in particular from the application WO2016185123. In other embodiments, as for example represented in FIG. 3A, the hybrid module (CP) includes a first scintillator crystal plate (P1) having a thickness less than the mean free path of the gamma ray in the crystal considered and a second scintillator crystal plate (P2) having a thickness greater than or equal to the mean free path of the gamma ray in the crystal considered and making it possible to absorb at least 50% of the energy of the gamma radiation, said second plate (P2) being separated from the plate P1 by a distance of at least 10 mm, preferably greater than the thickness of the thickest plate. In some embodiments, the pair of diametrically opposite modules is formed by two hybrid modules having these two types of plates. Such embodiments have the advantage of allowing very accurate time measurement between two opposite thin plates, for example as described in the application WO2017077164. Indeed, in a system that includes two hybrid modules facing each other and where these hybrid modules include a thin diffuser plate P1 and a thick absorber plate P2, the processing unit benefits from an improved time resolution (CRT) by measuring the accurate Times-of-Flight thanks to the events in coincidence between the 2 thin diffuser plates P1. Likewise, in some embodiments, as for example represented in FIG. 3D, at least part of the modules include a photo-detector (3) on each of the two opposite faces of each scintillator (2), which allows improving the time resolution and in particular facilitates the measurement of the depth with the photoelectric PET imaging. In some of these embodiments where the hybrid modules include two plates, the first plate (P1) is of chemical formula of the type ALnX3: Ce, A being any type of alkaline element, preferably of a type close to Cesium, Ln being a Lanthanide such as lanthanum or Cerium, X being a Fluoride such as Chlorine, Fluorine or Bromine.

Figure 3A:
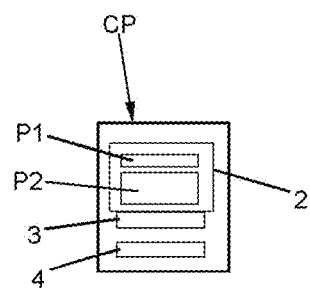
Figure 3B:
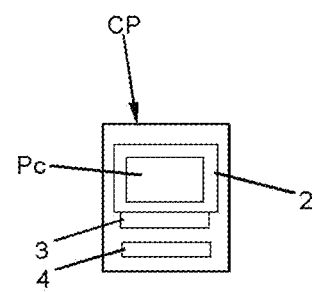
Figure 3C:
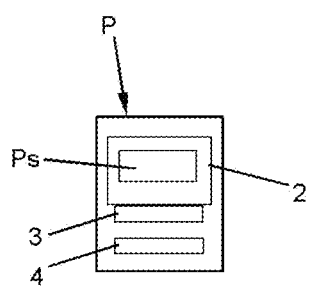
Figure 3D:
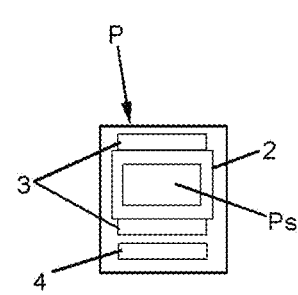
Figure 3E:
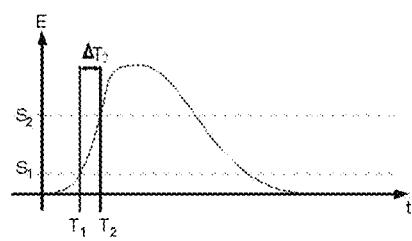
Figure 3F:
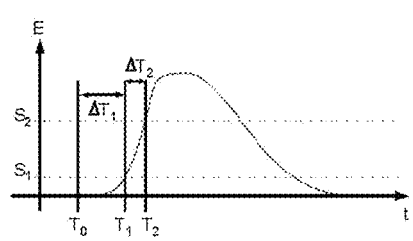

In some embodiments, for example as represented in FIG. 3C, at least one module of said pair is a "simple" module (P) capable only of a PET-type imaging by coincidence detection. Such a module then generally includes a scintillator crystal plate (Ps) having a thickness greater than or equal to the mean free path of the gamma ray in the crystal considered and making it possible to absorb at least 50% of the energy of the gamma radiation. It should also be noted that this plate (Ps) may be substantially of the same type as the second plate (P2) in the scintillators (2) of the two-plate hybrid modules (CP).

The present application can also relate to various embodiments of a system and/or a method using at least one "double threshold". These various embodiments are independent but not exclusive of the embodiments in which the system uses a frame as described in the present application and/or a combination of PET-type and Compton-type detectors. In such embodiments, advantage is taken of the use, by the processing unit, of a double threshold on the measurement of the time at which a certain amount of energy/photons has been detected on a pixel to overcome some drawbacks of the prior art, in particular regarding the monolithic crystals and the analog photo-detectors, for example as explained in the preamble of the present application. Thus, various embodiments relate to a system for imaging by gamma radiation detection comprising at least one processing unit (5) analyzing at least one signal provided by at least one set of detection modules (CP, P) mounted on at least one frame (1), each of the modules comprising at least one scintillator (2) emitting photons, when subjected to the influence of said gamma radiation, and at least one photo-detector (3) generating said signal (S) in response to said photons emitted by said scintillator (2), the system being characterized in that
said scintillator (2) is a monolithic scintillator crystal;
said photo-detector (3) is an analog photo-detector (3) whose analog signal provides a measurement representative of the photons detected (i.e., number and/or energy) by said monolithic scintillator (2) over time;
said acquisition device (4) is configured for the detection and filtering of the scintillation events thanks to an algorithm allowing it to measure a first time (T1) at which said analog signal exceeds a first threshold (S1) representative of the first photon detected and to measure a second time (T2) at which said analog signal exceeds a second threshold (S2) representative of a number n of detected photons, then to calculate the period ($\Delta T2$) that separates the first (T1) and the second (T2) time.

In practice, the photo-detector actually includes a plurality (i) of pixels which all provide an analog signal that the acquisition device (4) transmits to the processing unit (5). It is therefore understood that the acquisition device (4) actually performs a counting and the filtering calculation on each of the (i) pixels.

Preferably, this pre-processing of calculating the periods allowing the detection and filtering of the events must be done "on the fly" by the acquisition device (4), for example implemented in the form of an ASIC or an FPGA, because the periods are very fast (for example less than 10 ns) and this filtering would very probably be ineffective if it had to be carried out by the processing unit (5) which can for example be a PC or a remote server. It is understood from the foregoing that the present application proposes to measure the times at which the signal exceeds a first threshold in order to attempt to determine the time of arrival of the first photon, then a second threshold in order to determine the time at which the signal will have reached a sufficiently significant value to be truly representative of a scintillation event and not of the noise (e.g., electronic noise).

Methods for filtering the signal using a detection threshold are known in the prior art, as for example in the article by Frach et al. "The Digital Silicon Photomultiplier—Principle of Operation and Intrinsic Detector Performance" IEEE Nuclear Science Symposium Conference Record (pp. 1959-1965) 2009, N28-5. However, in these methods, a calculation of the integral of the signal over a fixed duration is generally used, in order to simply determine whether the signal exceeds a determined energy during that duration, without worrying about the exact time or the shape of the signal. In the present application, on the contrary, it is proposed to use the instantaneous energy and to determine the time at which this energy exceeds a threshold. Thanks to the two thresholds (S1, S2), the present application allows calculating the slope of the signal, which allows comparing the signal collected with known emission models for the scintillator crystals and with simulations of the spatial distribution of the photons by using these models.

In some embodiments, the acquisition device (4) collects the signal from the scintillator (2) on a plurality (i) of pixels and compares the time (T1) of the first photon detected on each of the i pixels, in order to determine the minimum value of this time on all the pixels and thus estimate the time (T0) of arrival of the first photon emitted by an event in the scintillator. It is understood that the acquisition device (4) therefore measures, for each of the i pixels, the difference ($\Delta T1$) between this time (T1) of this pixel and the minimum value of this time (T1) among all the pixels, which allows finding the pixel in which this time is the smallest and therefore estimating the time (T0) of arrival of the first emitted photon.

In some embodiments, said acquisition device (4) calculates a slope of rise of the signal between the two thresholds and eliminates the detected events whose rise slope is less than a determined value, in order to eliminate the noise of the signal and keep only validated scintillation events.

In some embodiments, said processing unit (5) establishes a map of the time of arrival of the photons from the events filtered by said acquisition device (4) to provide a first estimation of the position of a scintillation event and of a disk of non-scattered photons, then compares at least one model of the law of emission of the photons by the scintillator (2) with the number of photons detected in this disk at different times after the arrival of the first photon, in order to correct the diameter of this disc accordingly and therefore improve the accuracy of the measurement of the depth of the event.

In some embodiments, the processing unit corrects the probable delay between the measured and actual values of the time (T0) of arrival of the first emitted photon, by comparing these measured values with at least one model of the laws of emissions of the photons by the scintillator (2), preferably by taking into account the measurements of the times of arrival of the first and an $n^{th}$ photon in the adjacent pixels. This comparison can be done either by comparing T0 with the T1s of all the pixels, or by comparing T0 and T2 on the fastest pixel. It will be noted that reference is made here to a signal acquisition device that performs a pre-processing of the detected events in order to obtain validated/filtered events, then to a processing unit (5) that performs more complex calculations. In practice, the acquisition device (4) can be an Asic or a simple FPGA to calculate the thresholds and filter the events, while the processing unit (5) vectorizes the signals and requires greater calculation capacities, such as, for example, a large-size FPGA and/or computer resources (such as a computer, a server or possibly any other apparatus provided with sufficient computing resources).

The model of the emission law is based on the knowledge of the emission curves of the various types of scintillator crystals which can be used in the present invention and at least some of which are described in the present application. Such curves have in particular been described in the article by Seifert et al 2012 JINST 7 P09004.

Thus, some embodiments of the invention may also relate to a method for imaging by gamma radiation detection within a system comprising at least one processing unit (5) analyzing at least one signal provided by at least one set of detection modules (CP, P) mounted on at least one frame (1), each of the modules comprising at least one monolithic scintillator crystal (2) emitting photons, when subjected to the influence of said gamma radiation, at least one analog photodetector (3) whose analog signal provides a measurement representative of the energy of the photons emitted by said monolithic scintillator (2) over time and at least one acquisition device (4) collecting said signal to transmit it to said processing unit (5), the method being characterized in that it includes:
- the measurement of a first time (T1) at which said analog signal exceeds a first threshold (S1) representative of the first detected photon;
- the measurement of a second time (T2) at which said analog signal exceeds a second threshold (S2) representative of a number n of detected photons;
- the calculation of the period ($\Delta T2$) that separates the first (T1) and the second (T2) time.

In some embodiments, the method includes a collection of the signal from the scintillator (2), by the acquisition device (4), on a plurality (i) of pixels then a comparison ($\Delta T1$) between the time (T1) of the first photon detected on each of the i pixels, in order to determine the minimum value of this time on the set of the pixels and thus to estimate the time (T0) of arrival of the first photon emitted by the scintillator.

In some embodiments, the method includes the calculation, by said acquisition device (4), of a slope of rise of the signal between the two thresholds and eliminates the detected events whose rise slope is less than a determined value, in order to eliminate the signal noise and keep only validated scintillation events.

In some embodiments, the method includes an establishment, by said processing unit (5), of a map of the time of arrival of the photons from the events filtered by said acquisition device (4) to provide a first estimation of the position of a scintillation event and of a disc of non-scattered photons, then a comparison of at least one model of the law of emission of the photons by the scintillator (2) with the number of photons detected in this disc at different times after the arrival of the first photon, in order to correct the diameter of this disk accordingly and therefore to improve the accuracy of the measurement of the depth of the event.

In some embodiments, the method includes a correction by said processing unit (5), the processing unit corrects the probable delay between the measured and actual values of the time of arrival of the first photon (T0), by comparing these values measured with at least one model of the laws of emissions of the photon by the scintillator (2), preferably by taking into account the measurements of the times of arrival of the first and $n^{th}$ photon in the adjacent pixels.

It will be noted that the method can also be described as follows, without being interpreted as limiting the scope of the application. The first threshold per pixel (S1) is set as low as possible 1 to 2 photoelectrons. This threshold is used to measure the CRT and measure the relative time of illumination of the pixels in order to identify the circle of the non-scattered photons and the Compton interactions. This low threshold imposes a high level of noise that must be filtered. Only the accurate time of the first pixel (T0) detected must be known with accuracy. There is an interest only in the difference ($\Delta T1$) in the illumination time with the other pixels (T1–T0). The second threshold (S2) is mainly used to estimate the initial density of photons per pixel and to filter the relevant events. $\Delta T2$ (T1–T2) will be used for the reconstruction. It is also used for the filtering of the events. This second threshold should be adjustable, probably between 5 and 20 photoelectrons and depending on the type of crystal and on the energy of the interactions of interest. The range of adjustment must be significant because it allows capturing or turning off the low-density areas of the light distribution. The period for the crossing of the threshold must also be adjustable: At the shortest 1 ns, preferably 2.5 ns and at the longest 50 ns, preferably 20 ns. The light integration time to calculate energy must be adjustable. Today for example for CeBr3, 50 ns, 100 ns or 200 ns could be envisaged.

Filtering of the events:
An adjustable time threshold of the validation period is applied at each pixel
If $\Delta T2$ (T2–T1)<threshold=accepted event
If $\Delta T2$ (T2–T1)>threshold=rejected event
The value of the minimum period must be <50 ns (2.5 ns being an ideal value, but it is preferable to have several possible values)
At the second threshold, an event validation is required. An event is valid if n pixels have crossed the threshold, as defined above. (n=4 to 60 . . . adjustable and depending on the type of crystal).
The period between T0 (first pixel detected) and T1 (crossing of the threshold at 1 Phe on tile i) corresponds to the time distribution of the event.
The period between T1 and T2 serves as a threshold to accept/reject the event and also to improve the time accuracy of the reconstruction of time and of the circle of the non-scattered photons (post processing).

The present application describes various technical characteristics and advantages with reference to the figures and/or to various embodiments. Those skilled in the art will understand that the technical characteristics of a given embodiment can actually be combined with characteristics of another embodiment unless the opposite is explicitly mentioned or unless it is obvious that these characteristics are incompatible or unless the combination does not provide a solution to at least one of the technical problems mentioned in the present application. In addition, the technical characteristics described in a given embodiment can be isolated from the other characteristics of this mode unless the opposite is explicitly mentioned. It should be obvious to those skilled in the art that the present invention allows embodiments in many other specific forms without departing from the field of application of the invention as claimed. Consequently, the present embodiments should be considered by way of illustration, but may be modified within the field defined by the scope of the appended claims, and the invention should not be limited to the details given above.

The invention claimed is:

1. A system for imaging by gamma radiation detection comprising at least one processing unit analyzing at least one signal provided by at least a set of detection modules (CP, P) mounted on at least a frame, each of the modules comprising at least one scintillator emitting photons, when subjected to the influence of said gamma radiation, at least one photo-detector generating said signal (S) in response to said photons emitted by said scintillator and at least one acquisition device which collects said signal to transmit it to said processing unit, the system wherein: said frame comprises a plurality of locations distributed along at least one portion of two spherical caps facing each other and defining an imaging volume inside the system, said caps being separated by a distance (D) that allows accommodating an object (O) to be imaged in said volume; said frame being open, on at least one side between the two caps, so as to leave free access to said object (O) to be imaged in said volume; said set of detection modules (CP, P) includes at least one module of Compton camera type, having a field of view (CV) directed between the two caps and whose scintillator comprises at least one plate of scintillator crystal (P1) called fast scintillator crystal, whose time of rise to the light peak is less than 1 ns, so that this module is able to produce an image by using the Compton scattering; said set of detection modules (CP, P) includes at least one pair of coincidence detection PET modules, diametrically opposite to each other on said frame, each on one of the two caps, and defining an imaging axis (A), said processing unit analyzes the signal derived from said Compton-type module to determine the intersection of said imaging axis (A) with said field of view (CV) and to determine the optimal orientations and/or locations of the various detection modules (CP, P) within said caps of the frame so that the imaging axis (A) passes through the source of said gamma radiation in said object (O) to be imaged.

2. The system according to claim 1, wherein the system further includes at least one motor (M), driven by said processing unit and controlling the mobility of at least one of said detection modules (CP, P) on said frame and/or of the object to be observed inside said volume to obtain said orientations and/or said optimum locations defined by said processing unit.

3. The system according to claim 2, wherein at least one of said sets of detection modules (P, CP) actually includes only two modules, thanks to a first module (CP), called "hybrid" module, whose scintillator comprises at least one plate (P1) of scintillator crystal, called fast scintillator crystal, whose time of rise to the light peak is less than 1 ns, called "hybrid" module being able to produce both a Compton scattering and an absorption of at least part of the gamma radiation for a detection of coincidence between the events in this first hybrid module (CP) and the events in a second detection module (CP, P) with which this first hybrid module (CP) therefore forms said pair of coincidence detection PET modules.

4. The system according to claim 3, wherein said second detection module (CP, P) of each set is either also a hybrid module (CP) or a module (P), called "PET" module, able to produce only a photoelectric absorption for a detection of coincidence of events compared to the other detection module with which it forms said pair of coincidence detection PET modules.

5. The system according to claim 3, wherein each set includes several second modules (CP, P) facing the first hybrid module (CP) which is orientable by said motor (M) to align the imaging axis (A) between said hybrid module (CP) and either of these second modules (CP, P).

6. The system according to claim 3, wherein said motor (M) is able to move at least said second module (CP, P) on said frame, to place it facing the first hybrid module (CP) which is oriented by said motor (M) to align the imaging axis (A) between the first and the second module.

7. The system according to claim 3, wherein the first and the second module are both hybrid modules (CP) at least one of which is orientable and at least one of which is movable on the frame, by said motor (M).

8. The system according to claim 1, wherein said signal processing unit analyzes the signals derived from each set of detection modules (CP, P) and determines both the Compton scattering events and the photoelectric absorption events, to obtain the three-dimensional position, the energy and the time sequence of the Compton and photoelectric interactions of the gamma radiation in the volume between the detection modules (CP, P) of each set.

9. The system according to claim 8, wherein the processing unit calculates the Time-of-Flight of the photons between the two modules of the PET module pair, first hybrid module (CP) and second module (CP, P), to measure the depth of the source of gamma radiation in the object (O) to be imaged.

10. The system according to claim 9, wherein the processing unit uses the signal of at least one module pair of Compton camera type to combine their Compton imaging and carry out a triangulation in order to measure the depth of the source of gamma radiation in the object (O) to be imaged.

11. The system according to claim 1, wherein:
said scintillator is a monolithic scintillator crystal;
said photo-detector is an analog photo-detector whose analog signal provides a measurement representative of the energy of the photons emitted by said monolithic scintillator over time;
said acquisition device is configured for the detection and the filtering of the scintillation events thanks to an algorithm allowing it to measure a first time (T1) at which said analog signal exceeds a first threshold (S1) representative of the first detected photon and to measure a second time (T2) at which said analog signal exceeds a second threshold (S2) representative of a number n of detected photons, then to calculate the period ($\Delta$T2) that separates the first (T1) and the second (T2) time.

12. The system according to claim 11, wherein said acquisition device collects the signal from the scintillator on a plurality (i) of pixels and compares the time (T1) of the first photon detected on each of the i pixels, in order to determine the minimum value of this time on all the pixels and thus to estimate the time (T0) of arrival of the first photon emitted by the scintillator.

13. The system according to claim 11, wherein said acquisition device calculates a slope of rise of the signal between the two thresholds and eliminates the detected events whose rise slope is less than a determined value, in order to eliminate the signal noise and to keep only validated scintillation events.

14. The system according to claim 11, wherein said processing unit establishes a map of the time of arrival of the photons from the events filtered by said acquisition device to provide a first estimation of the position of a scintillation event and of a disk of non-scattered photons, then compares at least one model of the law of emission of the photons by the scintillator with the number of photons detected in this disk at different times after the arrival of the first photon, in order to correct the diameter of this disk accordingly and therefore improve the accuracy of the measurement of the depth of the event.

15. The system according to claim 11, wherein the processing unit corrects the probable delay between the measured and actual values of the time of arrival of the first photon (TO), by comparing these measured values with at least one model of laws of emissions of the photons by the scintillator, preferably taking into account the measurements of the times of arrival of the first and $n^{th}$ photon in the adjacent pixels.

* * * * *